(12) United States Patent
Ellard et al.

(10) Patent No.: US 6,458,068 B1
(45) Date of Patent: Oct. 1, 2002

(54) APPARATUS FOR DETERMINING THE POSITION OF RADIOACTIVE SEEDS IN NEEDLES USED FOR RADIOACTIVE SEED THERAPY FOR PROSTATE CANCER

(75) Inventors: Terence R. Ellard, Seattle; Stephen Knudsen, Bainbridge Island, both of WA (US)

(73) Assignee: Real World Design and Development Company, Seattle, WA (US)

( * ) Notice: Subject to any disclaimer, the term of this patent is extended or adjusted under 35 U.S.C. 154(b) by 0 days.

(21) Appl. No.: 09/621,169

(22) Filed: Jul. 21, 2000

(51) Int. Cl.[7] .................................................. A61N 5/00
(52) U.S. Cl. ............................................................ 600/1
(58) Field of Search ................................ 600/1, 2, 3, 4, 600/5, 6, 7, 8, 427, 407, 411; 250/370.11

(56) References Cited

U.S. PATENT DOCUMENTS 5,828,067 A * 10/1998 Rushbrooke et al. .. 250/370.11
6,129,670 A * 10/2000 Burdette et al. ............ 600/427

* cited by examiner

Primary Examiner—Kevin Shaver
Assistant Examiner—Brian Szmal
(74) Attorney, Agent, or Firm—Jensen & Puntigam, P.S.

(57) ABSTRACT

The apparatus for determining the position of radioactive seeds in a pre-loaded brachytherapy needle includes a pickup unit into which the loaded needle is inserted. A scintillating (phosphor) screen responsive to radiation from the seeds produces a light output of selected wavelength, which is then picked up by an optical array positioned along the screen. The resulting optical signals are then transmitted to a display assembly. The optical signals are focused and then applied to a CCD device. The output of the CCD device is processed by a microprocessor to produce a visual display of the radioactive seeds within the needle.

15 Claims, 7 Drawing Sheets

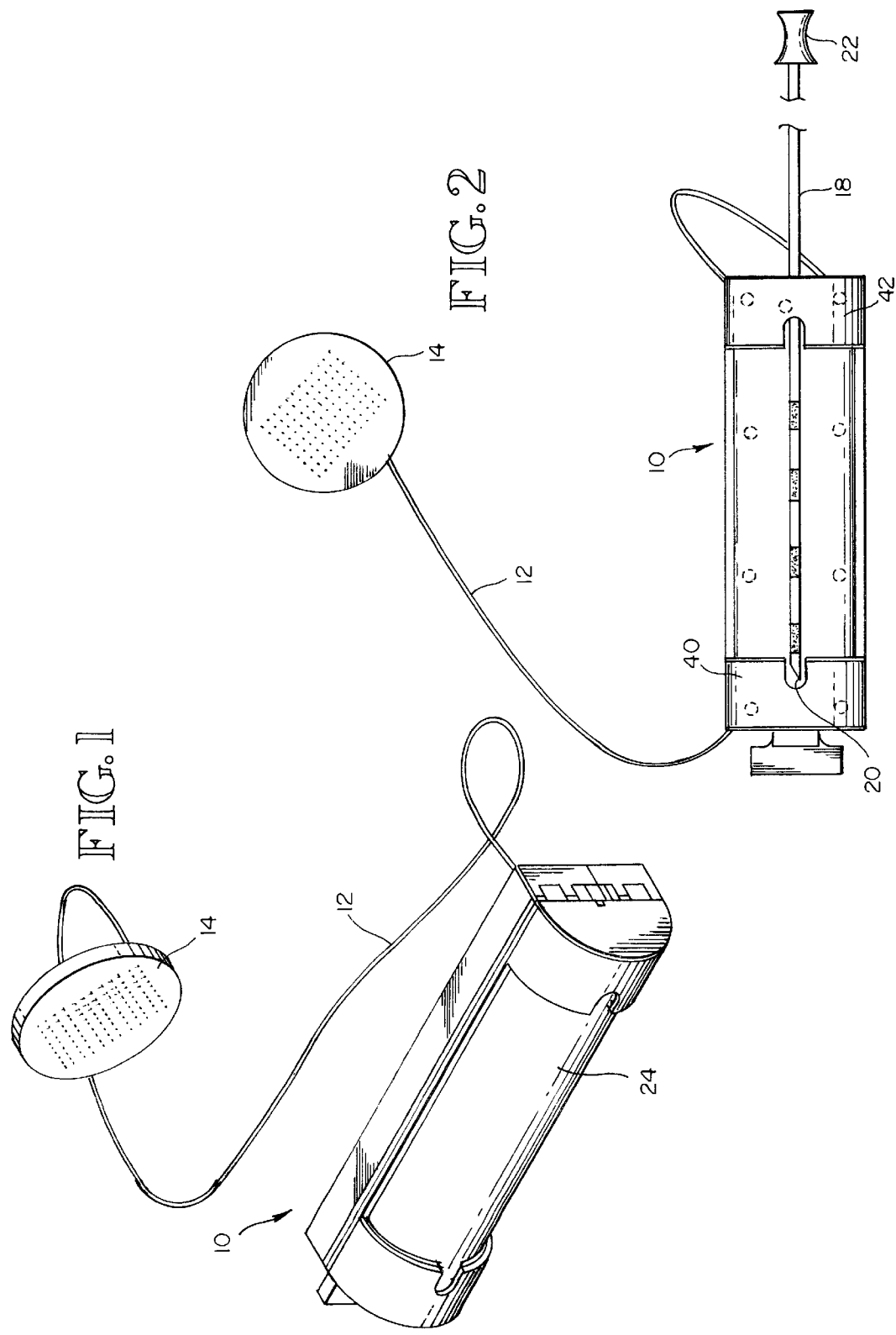

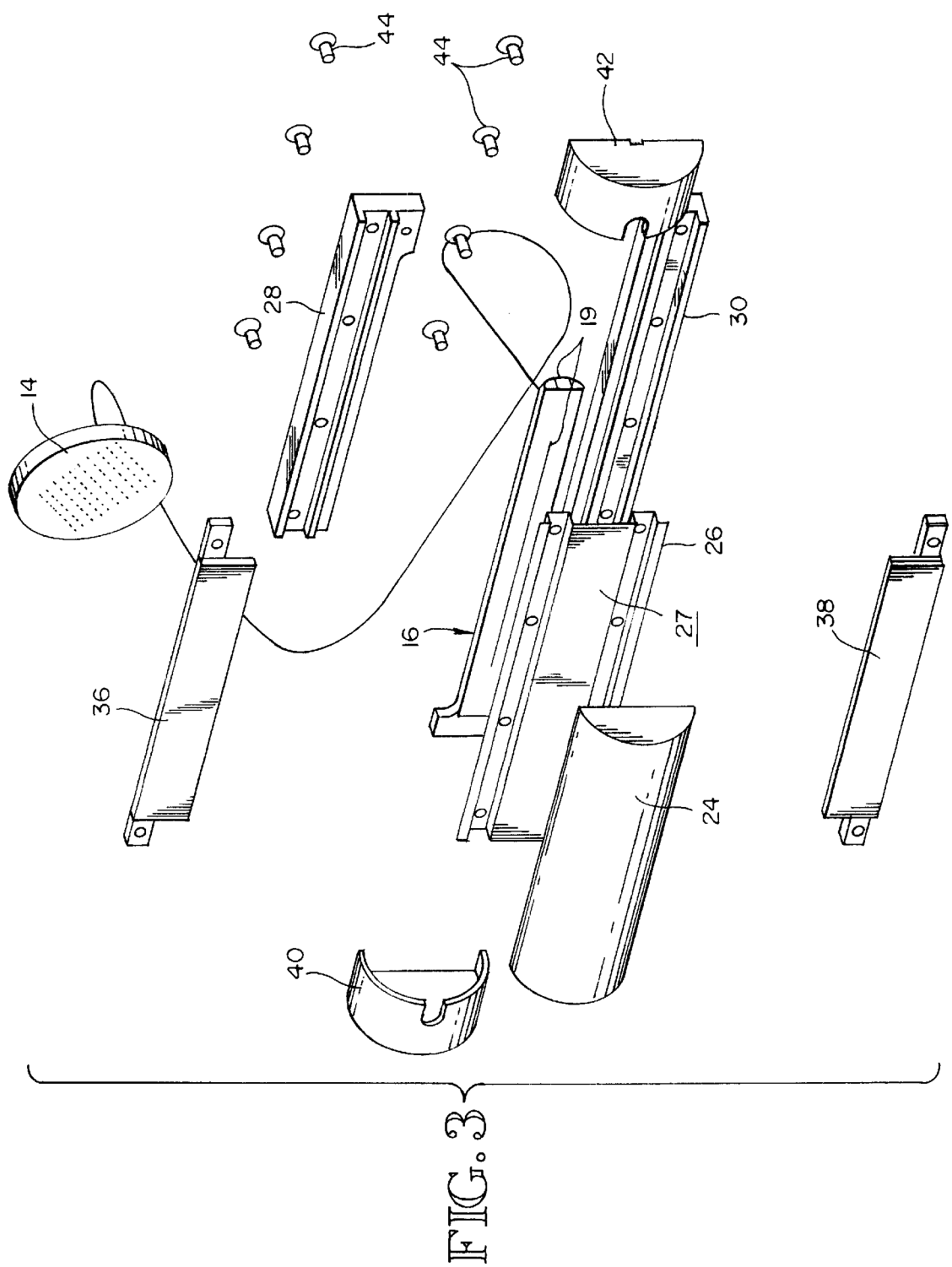

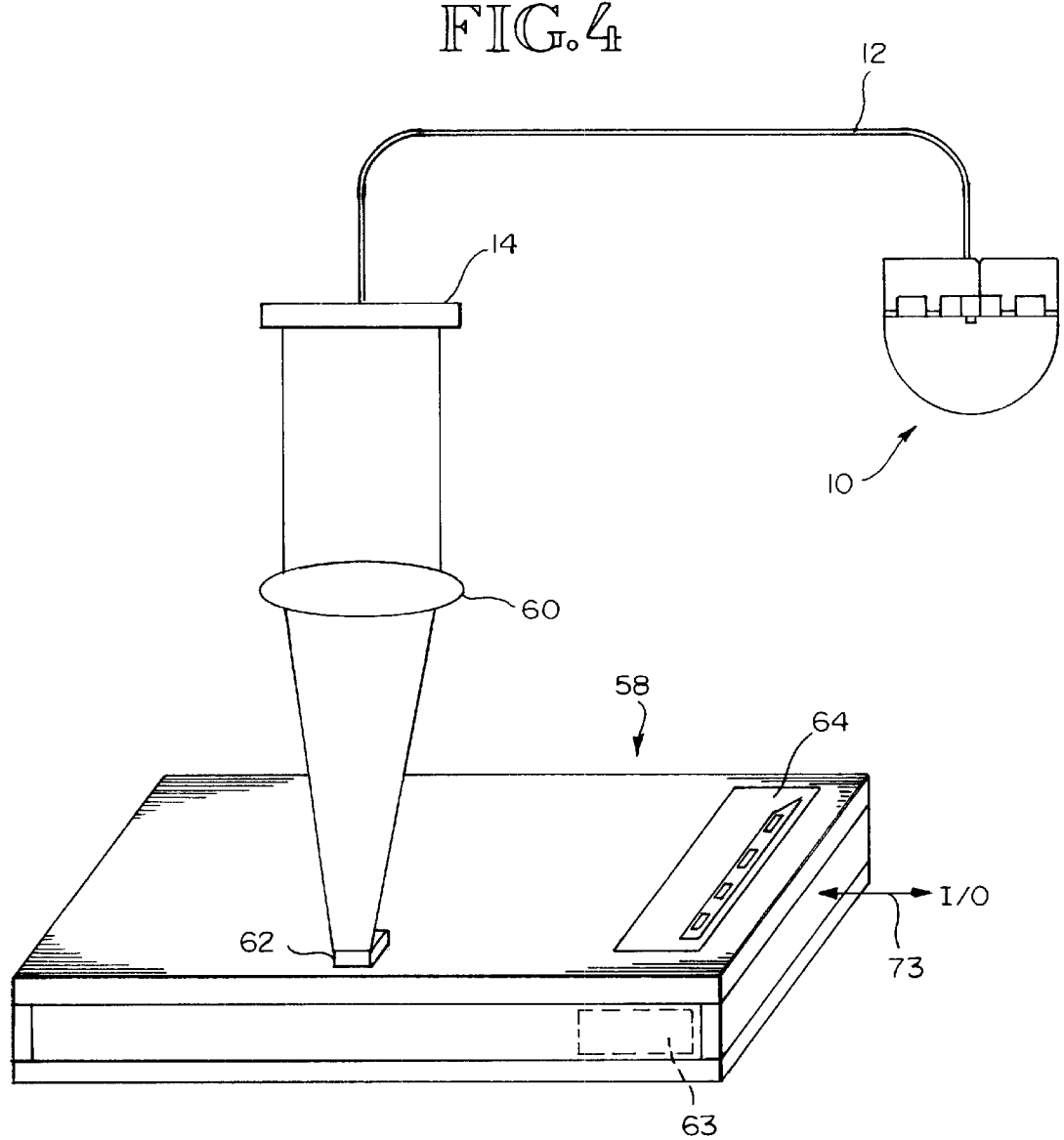

APPARATUS FOR DETERMINING THE POSITION OF RADIOACTIVE SEEDS IN NEEDLES USED FOR RADIOACTIVE SEED THERAPY FOR PROSTATE CANCER

TECHNICAL FIELD

This invention relates generally to radioactive seed therapy for prostate cancer and possibly other cancers, and more particularly concerns the determination of the position of radioactive seed and dosimetry in needles after the seeds have been loaded into the needles.

BACKGROUND OF THE INVENTION

In radioactive seed therapy for prostate cancer, referred to as brachytherapy, hollow stainless steel needles, typically 15 to 19 gauge, are loaded with cylindrical radioactive pellets, separated by inert spacers in a preselected pattern. The seed pattern is the result of a pre-procedure dosimetry plan to treat the prostate cancer in a given patient. The dosimetry plan is produced by ultrasound investigation of the prostate, identifying the location and configuration of the cancer within the prostate. The radioactive pellets are usually iodine #125 and/or palladium #103.

After the radioactive seeds have been loaded in the conventional stainless steel needles in the preselected pattern, it is not possible by visual inspection to verify the seed pattern and confirm that it is the correct pattern for that particular needle and/or whether the seeds have the desired radioactive strength. Such verification is in fact important in the overall treatment process, since errors do occur in loading and since sometimes the seeds are below the acceptable range of radioactive strength. To verify the radioactive seed pattern with conventional techniques, the loaded needle, prior to insertion in the prostate, is used to expose an X-ray film pack which is then developed and the resulting exposure compared with the dosimetry plan. However, this X-ray-based technique takes a substantial amount of time, is inconvenient and subject to error and thus is often not used.

Accordingly, it is desirable that a system be developed for conveniently and quickly verifying the radioactive seed pattern in loaded brachytherapy needles prior to use thereof.

SUMMARY OF THE INVENTION

Accordingly, the present invention is an apparatus for determining the position of radioactive seeds in a loaded needle, comprising: a pickup unit into which the loaded needle is positioned, the pickup unit including a detector element, such as a scintillating (phosphor) screen, positioned so as to be responsive to the radioactive energy from the seeds in the needle to produce a corresponding light output, the pickup unit further including an optical pickup assembly responsive to said light output to produce corresponding output information; and a display assembly, including a processor, responsive to the output information to produce a visual indication of the pattern of radioactive seeds in the needle, permitting convenient comparison with a preselected pattern of radioactive seeds therein.

BRIEF DESCRIPTION OF THE DRAWINGS

FIG. 1 shows a perspective view of a pickup/light generating portion of the system of the present invention.

FIG. 2 is a rear view of the apparatus of FIG. 1.

FIG. 3 is an exploded view of the apparatus of FIG. 1.

FIG. 4 is a perspective view showing the complete system of the present invention, including the portion of FIGS. 1–4.

BEST MODE FOR CARRYING OUT THE INVENTION

Figure 5:
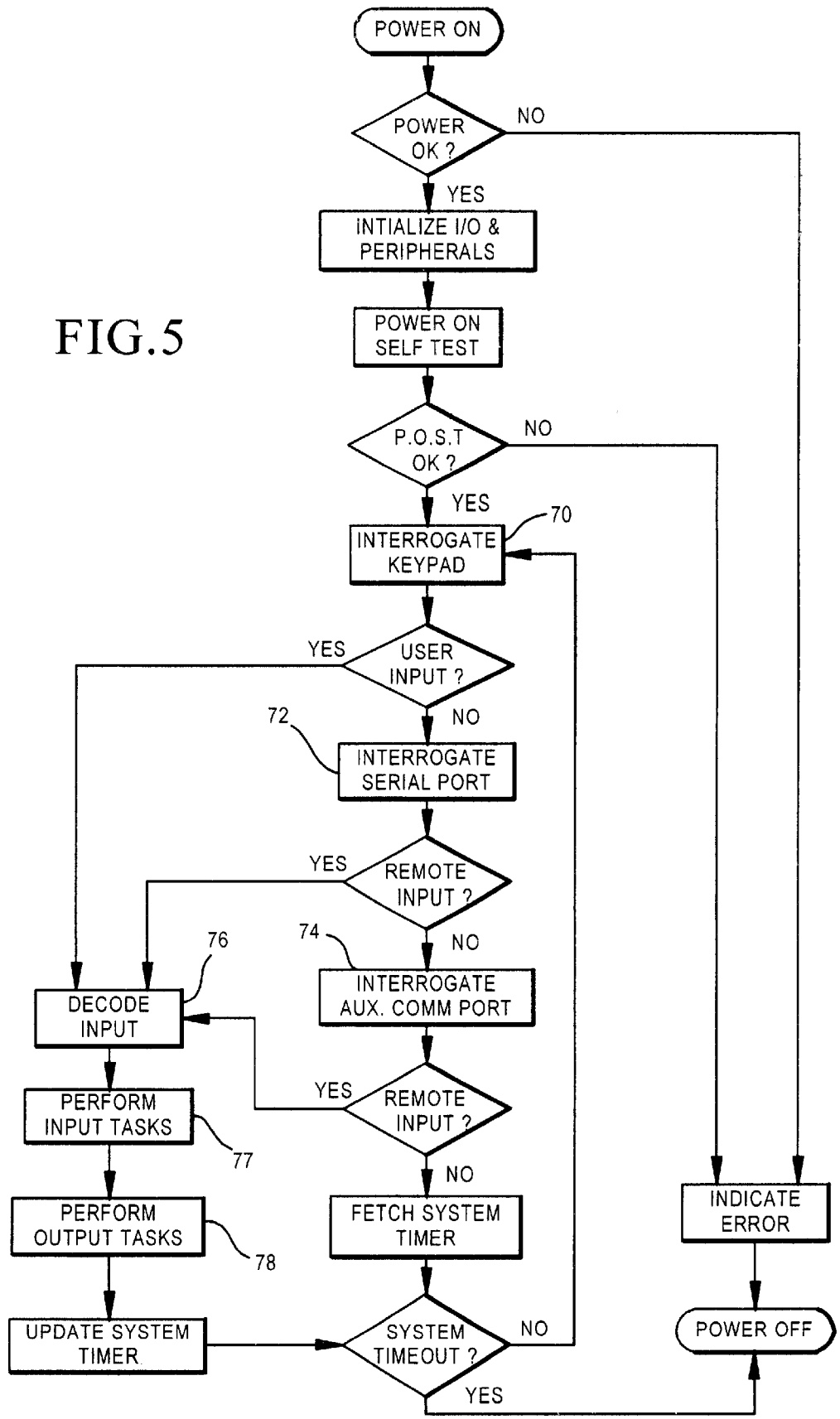
FIGS. 5 through 8 are flow charts showing the operation and software control of the system of the present invention.

FIGS. 1 through 4 show a pickup/light emitting portion of the seed position verification system of the present invention, said portion referred to generally at 10. This portion of the overall system detects the radiation of the seeds along the length of the needle, and produces a corresponding pattern of visible light, which is detected by a linear optical pickup assembly and then transmitted away from the pickup portion 10 via a fiber optic cable 12 to a two-dimensional optical matrix 14.

Pickup portion 10 includes a scintillating (fluorescing) screen 16 (FIG. 3) which detects radiation from a loaded brachytherapy needle 18 inserted into the apparatus. An optical pickup array 19 is positioned along the length of the screen 16. Screen 16 is approximately the length of that portion of the needle containing the radioactive seeds.

As briefly discussed above, a brachytherapy needle 18 is a stainless steel hollow needle, typically 16–19 gauge, with a sharp point at one end 20 and a small insertion handle 22 at the other end. Typically, the internal diameter of the needle is approximately 0.042 inches. Needle 18 is loaded with radioactive seeds and spacers, arranged to produce a particular pattern of radiation, in accordance with a dosimetry pattern or plan for the treatment of the prostate cancer. The pattern of seeds/spacers in a particular needle will depend upon the desired radiation effect for the particular location in the prostate in which the needle is to be inserted.

A more detailed description of the brachytherapy technique is discussed in U.S. Pat. No. 5,938,583 and in an article by Grimm, Blasko and Ragde referred to therein. Basically, brachytherapy involves a plurality of radiation seed-loaded needles, each of which is inserted into the prostate in a preselected location. The needles, typically numbering 30 for a given procedure, are positioned in accordance with a dosimetry plan for treatment of the prostate cancer of a particular patient. The radioactive seeds loaded into the needle can be of various radioactive materials, but are usually Iodine #125 and Palladium #103. There may be different types of radioactive seeds in a single needle, to produce different radiation strengths at different portions of the needle. The particular pattern of seeds and spacers in the needle depends upon the desired dosimetry plan for the particular patient.

Referring again to FIGS. 1–4 relative to verifying the load pattern in brachytherapy needles, a loaded brachytherapy needle 18 is inserted into one end of pickup portion 10, as shown most clearly in FIG. 2. Referring now to FIG. 3, pickup portion 10 includes a hemispherical member 24 which is made from leaded acrylic, through which the inserted needle is visible. Behind hemispherical portion 24 is a stainless steel shield element 26. The inserted needle is positioned adjacent surface 27 of shield 26. Secured to the upper and lower longitudinal portions of the opposing surface of shield 26 are two elongated upper and lower frame elements 28 and 30. Positioned between the two frame elements is the scintillating screen 16. The shield 26 protects the screen 16 from the needle 18.

Screen 16 is responsive to the high energy (X-ray and gamma radiation) from the radioactive seeds in the needle to produce visible light. In the present embodiment, the visible light is approximately 550 nanometers (green). Other screens, however, could be used to produce different light wavelengths. The linear optical pickup array 19 detects the light from the screen 16. The pickup array includes a plurality of individual detectors in screen 16, each of which is connected to an optical fiber, which are bundled together to form the fiber-optic cable 12, for transmission of the detected light away from pickup unit 10.

Upper and lower longitudinal frame members 36 and 38 positioned between shield 26 and hemispherical member 24 and two hemispherical end caps 40 and 42 complete pickup portion 10. A space between the frame members 36 and 38 accommodates the inserted needle, so that the needle is visible through leaded acrylic member 24. Eight small bolts 44 hold the various pickup portion elements 26, 28, 30, 36, 38 together. The combination of screen 16 and optical pickup assembly 19, as indicated above, is held securely between frame elements 28 and 30. The various frame elements and the shield have particular cross-sectional patterns, as shown most clearly in FIG. 3, which result in them mating together in a particular manner. The frame elements 28 and 30 are arranged and configured so that a loaded needle can be conveniently inserted into the pickup portion, to come adjacent shield 26.

After the loaded needle has been inserted into the pickup unit, it is visible through acrylic member 24. This allows the operator to insure that the loaded needle which is to be inspected is properly inserted into the pickup unit. As indicated above, the needle is inserted adjacent surface 27 of shield 26. Optical array 19 is responsive to the light emitted from screen 16. A plurality of individual optical fibers transmit light from the individual pickup elements in the array away from pickup portion 10. The presence/absence of light in the various optical fibers along the array represents the pattern of seeds and spacers in the needle.

The optical information from the linear pickup array 19 is transmitted through the plurality of optical fibers, combined into fiber-optic cable 12, to a two-dimensional optical matrix 14 in the embodiment shown. Referring to FIG. 4, the output from the two-dimensional optical matrix 14 is applied to a display assembly 58 via a focusing lens 60, the output of which is applied to a conventional CCD (charge coupled device) pickup unit 62. The output from CCD 62 is then processed by the display assembly microprocessor 63 in the display assembly 58 to produce a visual display 74 which shows the position of the radioactive seeds within the needle. The visual display 74 can be compared to a chart of the actual desired pattern of seeds within the needle to determine the correlation between the two. If not, corrective action to the loaded needle can be taken. FIG. 4 shows a visual display 74 with four radioactive seeds indicated. The dosimetry plan for the patient can be stored in a computer away from assembly 58 and then compared automatically by processor 63 against the results it has determined from the optical information and which it used to produce the display 74. Results of the determination can then be provided, i.e. displayed.

A numerical indication of the strength and/or type of seed can also be provided in the visual display (not shown in FIG. 4). This information is also produced by the processing circuit 63 in response to the optical information from the pickup array 19 through fiber-optic cable 12 and the CCD 62 to the display assembly. If the strength of the radiation from a particular seed is not within the prescribed range, e.g. lower than the prescribed threshold, then that condition can be corrected by replacing the seed. Heretofore, there was no way to accurately determine seed strength after the needle had been loaded. Similarly, if the pattern of different types of radioactive seeds is other than as it should be, corrective action can be taken. All of the information about the seed pattern, including the visual display information, the seed strength and the type of seed, as well as the results of any automatic comparison, can be stored in memory, either in the display assembly or in a computer or similar device, away from the display assembly.

Hence, the accurate loading of a needle for brachytherapy can be quickly confirmed by inserting the loaded needle into the pickup unit and then comparing the visual display 64 produced by the visual display processor 63, with the desired seed pattern and strength. This invention thus solves a troublesome problem in the art by accurately and quickly verifying the loading pattern of the needle prior to its use in brachytherapy.

As an alternative to the optical arrangement shown in FIGS. 1–4, which includes a linear optic pickup, a fiber optic cable, a lens, and a CCD pickup unit, a pin diode linear array could be used. The pin diode array is directly responsive to the light output from the scintillating screen 16 to produce an electrical signal output which can be routed directly to a microprocessor, which would eliminate the need for the light path/CCD input approach of FIGS. 1–4. The analog output from the linear pin diode array is converted to a digital signal by an A/D converter in the microprocessor 63, and then processed to produce the desired visual display. This embodiment has some advantages over the fiber-optic cable and lens arrangement.

In another embodiment, CCD units could be positioned along both sides of the needle, alternating (and slightly overlapped), from side to side, for the length of that portion of the needle which includes the seeds. The CCD units could be used to detect light from a phosphor (scintillating) screen or phosphor could be deposited directly on the CCD.

FIGS. 5–8 show flow charts for software control of the system. The flow charts and the software itself are routine and the result of ordinary skill, given information about the system and its basic operation outlined above. FIG. 5 is the flow chart for the main routine in the microprocessor 63. After the power is turned on, a number of self-diagnostic tests are performed to ensure proper operation of the system. If the power-on, self-test (p.o.s.t.) tests are OK, then various input sources for the system are interrogated. In the simplest arrangement of the system of the present invention, the pickup portion 10 will be self-initializing upon the insertion of the loaded needle. However, in a more sophisticated embodiment, input information and commands can be provided to the system, either through an input unit (keypad) on the display assembly itself or a computer (keyboard entry) or other peripheral device connected to the display assembly means via a serial port or a communication port. The display assembly typically includes a plurality of serial ports and communication ports.

These three input possibilities are shown at blocks 70, 72, and 74. In each case, the input (user generated) can be various key commands, interaction of a mouse-type control with a user interface screen (graphical user interface-GUI), voice recognition commands or needle motion input. Remote input can be software information or requests or information from dosimetry software, or from various sensors, i.e. fiber optic cable CCD, or pin diodes.

The input, from whatever source, is then decoded, as shown at block 76 and the requested input tasks (discussed above) and the output tasks can be performed, as shown at blocks 77 and 78. The output tasks include display of the actual seed location in visual format, seed strength, either in a graph or numerical form, seed type, i.e. iodine #125 or palladium #103 and, finally, results of an automatic comparison of the processed results with the prescribed treatment (dosimetry) plans. The system timer is then updated and a determination as to whether the system has timed out is made. If yes, the routine is over and power to the system is turned off. If there is no remote input, the system timer is interrogated (fetched) and a determination made as to system timeout. Generally, the system is designed to be quickly timed out if there is no input information.

Figure 6:
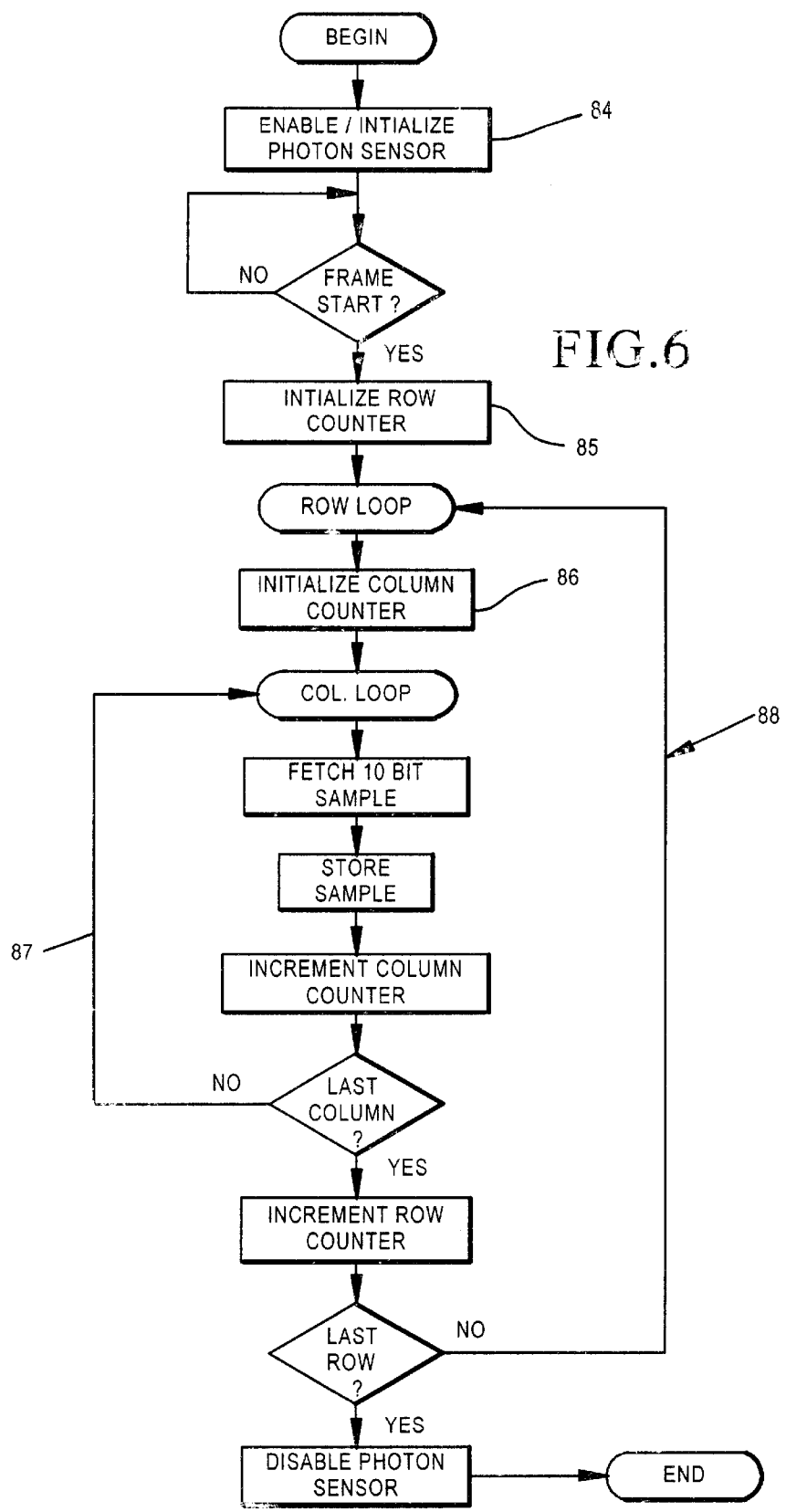

FIG. 6 shows the data acquisition subroutine for the two-dimensional array embodiment of FIGS. 1–4. After the pickup unit is initialized (block 84), the row and column counters are initialized (blocks 85 and 86) and then the optical information provided to array 14 is sampled, by columns and rows, as shown generally by column loop 87 and row loop 88. When the column/row sampling has been completed, the light pickup array is disabled.

Figure 7:
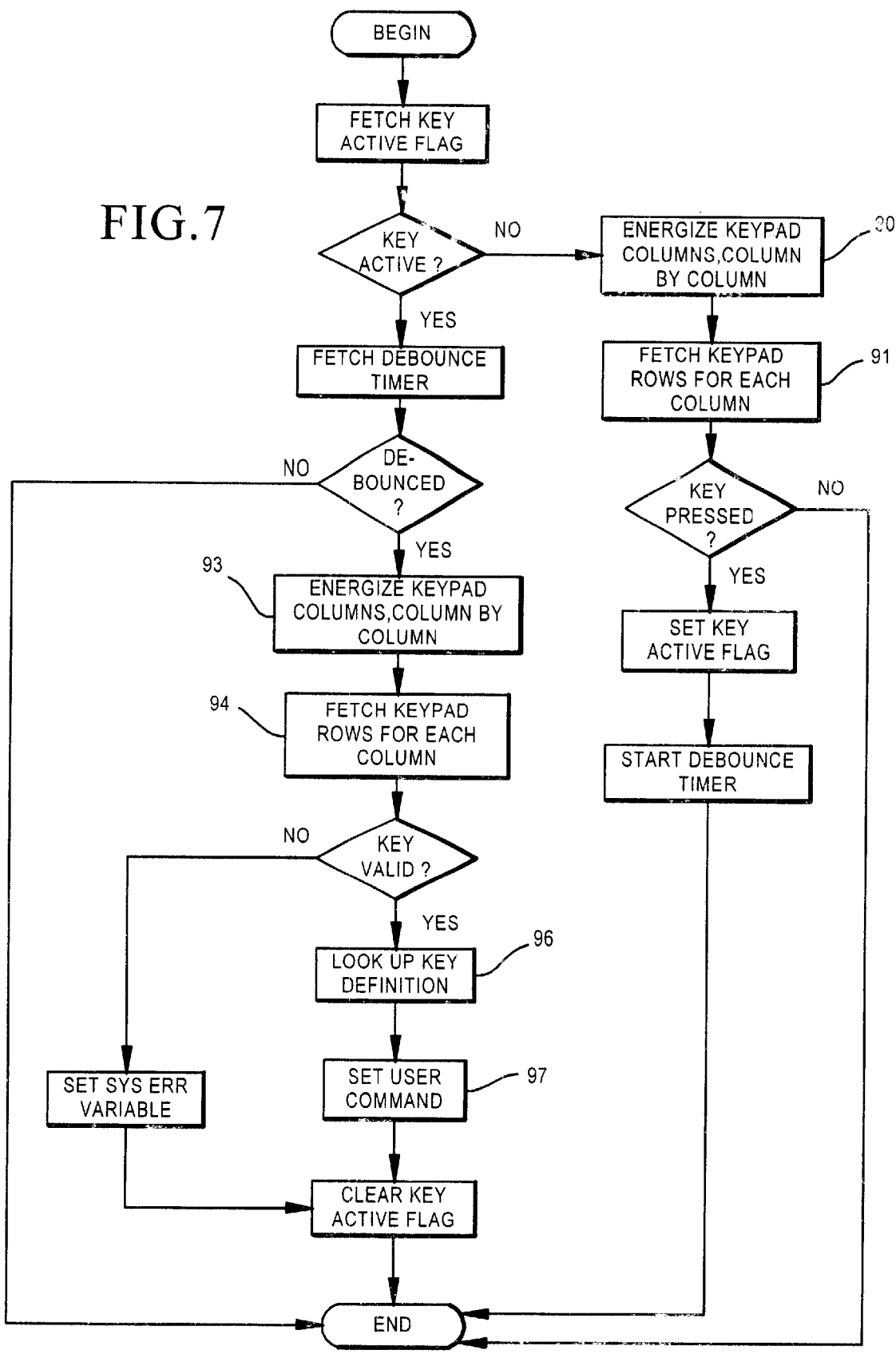

FIG. 7 shows a keypad interrogate subroutine, which is a specialized feature providing an input capability from the user on the display assembly. It could also be used with other keyboard-type output. The keypad is not a necessary component of the present invention, and is not included in FIG. 4. Basically, the routine begins with initialization of the keypad and determination of whether the keys are active. If not, the keypad columns are energized, column by column, and the keyboard rows are "fetched" (interrogated) (blocks 90 and 91) for each column. If a key has been pressed, a "key active" flag is set and the debounce timer is started.

If, on the other hand, the key is active, the debounced timer is interrogated and if the timer is debounced, then the columns of keys are energized (for interrogation) column by column, with each key row being interrogated for each column, to determine the keys which have been operated (blocks 93, 94). If a key has been operated, a look-up is made concerning the key and the corresponding user command is set (blocks 96, 97). After this is done, then the key active flag is cleared. If any system errors occur, as indicated by an invalid key, then the system error variable is set. At this point, the subroutine for the keypad ends. Again, it should be understood, however, that a keypad input is not a necessary component of the present invention. The system may be self-initializing and provide a visual output without additional input. Alternatively, input could be provided from a variety of sources, including a keypad.

Figure 8:
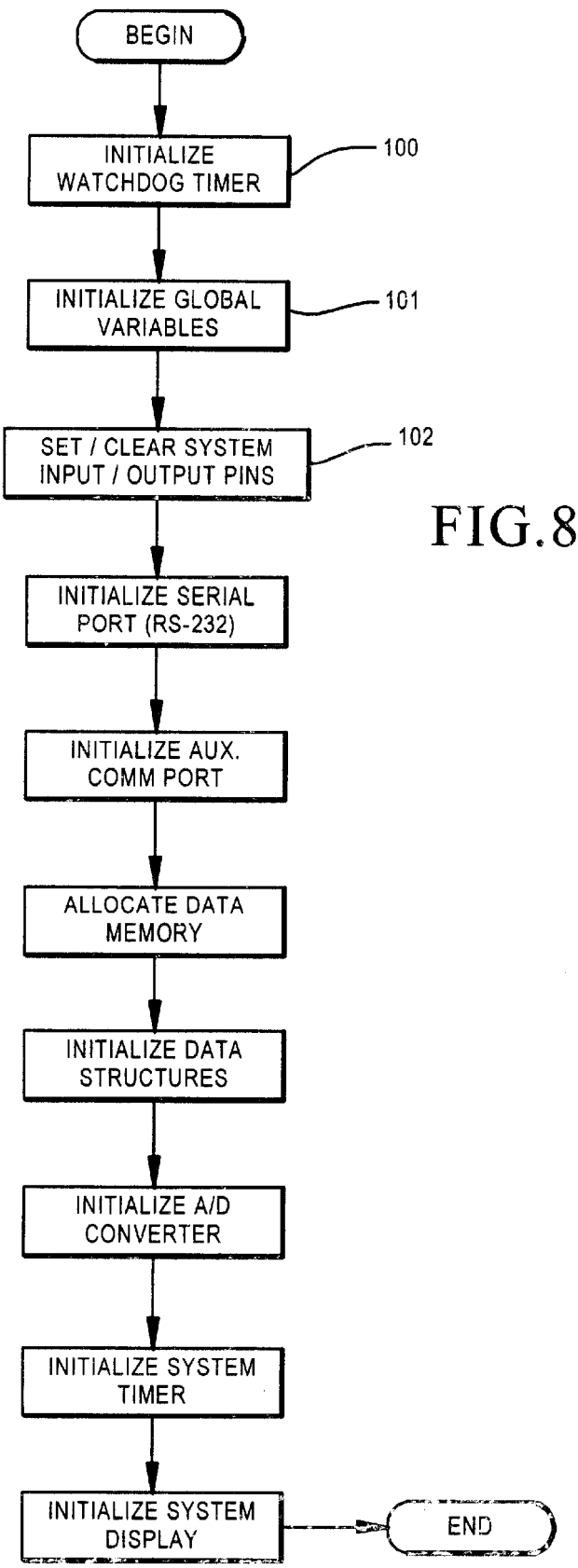

FIG. 8 shows an I/O and peripheral initialization subroutine. First, the variables in the system, including the timer, the global variables and the input/output pins, are initialized (blocks 100, 101, 102). The serial port(s) from the display assembly 58 to which any peripheral device is connected are then initialized, as well as the auxiliary communication port(s), as required. The data memory, data structures, A/D converter, system timer and system display assembly are then all energized in turn. This results in the visual display assembly being ready to communicate with peripheral devices and this subroutine then ends.

The control signals produced by processor 63 from the signals from the CCD can be used to produce the visual display seen in FIG. 4 on the display assembly 58 itself, or they can be routed through an input/output port of the display assembly 58 to a computer, a local network or even the internet. The existing system can support all of these possibilities. The control signals can then be used by an appropriate peripheral device to produce a visual display. The output options are integral to the onboard microprocessor, driven by either internal or external software.

A display on the external device, i.e. an external computer, or other display device connected to a network or the internet, will be substantially similar to the visual display shown on the device of FIG. 4. Information as to seed strength and seed type can also be displayed. As indicated above, external dosimetry software can be used to provide dosimetry information to processor 63 which can compare the dosimetry information with the information it produces concerning the actual pattern of seeds in the loaded needle. The results can be provided visually or printed out. The results of the present invention can also be stored, typically in peripheral storage, for later reference.

Thus, the present invention includes a pickup portion into which a loaded brachytherapy needle is conveniently inserted. The pickup portion produces an optical signal representative of the position of radioactive seeds within the needle. The optical information is transmitted over a fiber-optic cable to a display assembly, which includes a lens and a CCD pickup apparatus. The output from the CCD is processed and used to produce a display which shows visually the actual position of radioactive seeds within the needle, which can be compared with an existing dosimetry chart showing the desired seed pattern in the needle. The seed strength and type of seed can also be determined and displayed in some manner. If the visual display results do not correlate with the desired pattern, corrective action can be taken.

It should be understood that a preferred embodiment has been disclosed for purposes of illustration. For instance, it should be understood that the present invention is not limited to brachytherapy but can be used with needles loaded with radioactive seeds used in treatment of other cancers or conditions. Brachytherapy provides a specific context for the description of the invention. Changes and substitutions can be incorporated in the preferred embodiment without departing from the spirit of the invention which is defined by the claims which follow.

What is claimed:

1. An apparatus for determining the pattern of radioactive seeds in a preloaded needle, comprising:

a pickup unit, separate from and independent of a needle loading apparatus, into which the preloaded needle is positioned, the pickup unit including a detector element spaced away from the preloaded needle and positioned so as to be responsive to the radioactive energy from the seeds in the needle to produce a corresponding light output, the pickup unit further including an optical pickup assembly responsive to said light output to produce corresponding output information; and a display assembly, including a processor, responsive to the output information to produce visual indication information concerning the pattern of radioactive seeds in the preloaded needle, permitting convenient comparison with a preselected desired pattern of radioactive seeds therein.

2. An apparatus of claim 1, wherein the visual indication information includes a line-up of seeds and spacing elements, so that the position and number of seeds within the needle can be readily determined.

3. An apparatus of claim 1, wherein the strength of each seed in the needle is determined and an indication of said strength of each seed is provided.

4. An apparatus of claim 1, wherein the type of each seed in the needle is determined and an indication of said type of each seed is provided.

5. An apparatus of claim 1, including fiber-optic means for transmitting optical information from the pickup unit to the display assembly.

6. An apparatus of claim 5, wherein the apparatus further includes a lens for focusing the output information, and a CCD device for converting the focused optical information into an electrical signal for use by the processor.

7. An apparatus of claim 1, wherein the visual indication is displayed as part of the display assembly.

8. An apparatus of claim 1, wherein the visual indication is displayed on an external display apparatus and wherein the apparatus includes means for transmitting processor signals from the display assembly to the external display apparatus.

9. An apparatus of claim 8, wherein the external display apparatus is a computer monitor.

10. An apparatus of claim 1, wherein the processor includes means responsive to the preselected desired pattern of radioactive seeds in the needle and the determined pattern of radioactive seeds to automatically determine whether or not the determined pattern is identical to the desired pattern.

11. An apparatus of claim 10, including an indicator indicating the result of said determination.

12. An apparatus of claim 1, including a memory assembly for storing the visual indication information.

13. An apparatus of claim 12, wherein the memory assembly is located in a peripheral device.

14. An apparatus of claim 1, including a shield element positioned between the detector element and the positioned preloaded needle.

15. An apparatus of claim 14, wherein the shield is stainless steel.

* * * * *